(12) United States Patent
Rastashanskiy et al.

(10) Patent No.: US 11,219,641 B2
(45) Date of Patent: Jan. 11, 2022

(54) USE OF LITHIUM ASCORBATE TO PREVENT AND TREAT ALCOHOLISM AND ALCOHOL INTOXICATION

(71) Applicant: «NORMOPHARM» LIMITED LIABILITY COMPANY [RU/RU], Moscow (RU)

(72) Inventors: Vyacheslav Valerievich Rastashanskiy, Moscow (RU); Konstantin Sergeevich Ostrenko, Obninsk (RU); Olga Alexeevna Gromova, Moscow (RU)

(73) Assignee: «NORMOPHARM» LIMITED LIABILITY COMPANY, Moscow (RU)

( * ) Notice: Subject to any disclaimer, the term of this patent is extended or adjusted under 35 U.S.C. 154(b) by 0 days.

(21) Appl. No.: 16/631,835

(22) PCT Filed: Jul. 20, 2018

(86) PCT No.: PCT/RU2018/050081
§ 371 (c)(1),
(2) Date: Jan. 17, 2020

(87) PCT Pub. No.: WO2019/017825
PCT Pub. Date: Jan. 24, 2019

(65) Prior Publication Data
US 2020/0147128 A1 May 14, 2020

(30) Foreign Application Priority Data
Jul. 20, 2017 (RU) .................................. 2017126079

(51) Int. Cl.
A61K 33/00 (2006.01)
A61P 25/32 (2006.01)
A61K 31/375 (2006.01)

(52) U.S. Cl.
CPC ............ *A61K 33/00* (2013.01); *A61K 31/375* (2013.01); *A61P 25/32* (2018.01)

(58) Field of Classification Search
CPC ........ A61K 33/00; A61K 31/375; A61P 25/35
See application file for complete search history.

(56) References Cited

U.S. PATENT DOCUMENTS 7,449,598 B2   11/2008   Malkar et al.

FOREIGN PATENT DOCUMENTS

| RU | 2 351 326 | 4/2009 |
| RU | 2 618 394 | 5/2017 |

OTHER PUBLICATIONS

Dawson et al. Association between stress and drinking (2005).*
Ostrenko et al. (Pharmacokinetics and Pharmacodynamics 1(2017).*
Plotnikov et al. (Physiology and Pharmacology 19: 107-113; (2015).*
Basselin M. et al. Chronic lithium chloride administration attenuates brain NMDA receptor-initiated signaling via arachidonic acid in unanesthetized rats, Neuropsychopharmacology, 2006, vol. 31, N.8, pp. 1659-1674.
Basselin M. et al. Chronic lithium chloride administration to unanesthetized rats attenuates brain dopamine D2-like receptor-initiated signaling via arachidonic acid, Neuropsychopharmacology, 2005, vol. 30, N.6, pp. 1064-1075.
Castro L. et al. Central 5-HT2B/2C and 5-HT3 receptor stimulation decreases salt intake in sodium-depleted rats, Brain Research, 2003, vol. 981, N. 1-2, pp. 151-159.
Chang C-M. et al. Utilization of Psychopharmacological Treatment Among Patients With Newly Diagnosed Bipolar Disorder From 2001 to 2010, Journal of Clinical Psychopharmacology, 2016, vol. 36, N.1, pp. 32-44.
Darcq E. et al. MicroRNA-30a-5p in the prefrontal cortex controls the transition from moderate to excessive alcohol consumption, Molecular Psychiatry, 2014, pp. 1-11.
Diaz-Sastre C. et al. Cholesterol and lithium levels were correlated but serum HDL and total cholesterol levels were not associated with current mood state in bipolar patients, Journal of Clinical Psychiatry, 2005, vol. 66, N.3, pp. 399-400.
Ebstein R.P. et al. The effect of lithium on noradrenaline-induced cyclic AMP accumulation in rat brain: inhibition after chronic treatment and absence of supersensitivity, Journal of Pharmacology and Experimental Therapeutics, 1980, vol. 213, N.1, pp. 161-167 (Abstract).
Focosi D. et al. Lithium and hematology: established and proposed uses, Journal of Leukocyte Biology, 2009, vol. 85, N.1, pp. 20-28.
Hillert M.H. et al. Dynamics of hippocampal acetylcholine release during lithium-pilocarpine-induced status epilepticus in rats, Journal of Neurochemistry, 2014, vol. 131, N.1, pp. 42-52.
Koda L.Y. et al. Lithium treatment decreases blood pressure in genetically hypertensive rats, European Journal of Pharmacology, 1981, vol. 76, N.4, pp. 411-415.
Marx C.E. et al. Neuroactive steroids, mood stabilizers, and neuroplasticity: alterations following lithium and changes in Bcl-2 knockout mice, International Journal of Neuropsychopharmacology, 2008, vol. 11, N.4, pp. 547-552.
Myers R.D. et al. Neurotransmitter and neuromodulator mechanisms involved in alcohol abuse and alcoholism: Epitome of cerebral complexity, Neurochemistry International, 1995, vol. 26, N. 4, pp. 337-342.
Ostrenko K.S. et al. Determination of acute toxicity and adverse effects of high doses of prolonged use of lithium ascorbate on Wistar rats, Farmakokinetika i farmakodinamika, 2016, N.4, p. 44-54 (w/ English abstract).
Ostrenko K.V. et al. The effectiveness of lithium ascorbate on chronic alcohol intoxication model, Farmakokinetika i farmakodinamika, 2017, N.1, pp. 11-21 (w/ English abstract).

(Continued)

*Primary Examiner* — Shirley V Gembeh
(74) *Attorney, Agent, or Firm* — Nixon & Vanderhye PC

(57) ABSTRACT

The invention relates to medicine, particularly to the chemical and pharmaceutical industry and more particularly to the use of lithium ascorbate, in a dose of at least 5 mg/kg, as an agent for preventing and treating alcoholism and alcohol intoxication, and also providing protection of brain neurons and reducing demyelinating complications. The invention makes it possible to broaden the range of agents for this purpose.

7 Claims, 10 Drawing Sheets

(56) References Cited

OTHER PUBLICATIONS

Phelan K.M. et al. Lithium interaction with the cyclooxygenase 2 inhibitors rofecoxib and celecoxib and other nonsteroidal anti-inflammatory drugs, Journal of Clinical Psychiatry, 2003, vol. 64, N.11, pp. 1328-1334 (Abstract).
Pronin A.V. et al. Study of the pharmacokinetics and compartmentalization of lithium ascorbate, Young Scientist 2016, N.15, Aug., pp. 547-555 (w/ English abstract).
Stengaard-Pedersen K. et al. In vitro and in vivo inhibition by lithium of enkephalin binding to opiate receptors in rat brain, Neuropharmacology, 1982, vol. 21, N. 8, pp. 817-823.
Zawalich W.S. et al. Interactions between lithium, inositol and mono-oleoylglycerol in the regulation of insulin secretion from isolated perifused rat islets / Biochemistry Journal, 1989, vol. 262, N.2, pp. 557-561.

\* cited by examiner

USE OF LITHIUM ASCORBATE TO PREVENT AND TREAT ALCOHOLISM AND ALCOHOL INTOXICATION

This application is the U.S. National Phase of International Application No. PCT/RU2018/050081 filed Jul. 20, 2018, which claims priority to Russian Application No. 2017126079 filed Jul. 20, 2017, the entire content of each of which is hereby incorporated by reference in this application.

FIELD OF THE INVENTION

The present invention relates to the field of medicine and chemical and pharmaceutical industry, namely, to creation of an agent for prophylaxis and treatment of chronic alcohol intoxication.

BACKGROUND

Alcoholism remains one of the most vital social and medical problems in modern society. Alcohol abuse is the main factor of demographic and social crisis, national threat at the level of an individual, family, society, state. Presently, alcohol abuse in Russia leads to about 500 thousand premature deaths annually. [*Alcohol abuse in the Russian Federation: social and economic consequences and countermeasures/Report of the Commission on social and demographic policy of the Civic Chamber of the Russian Federation*/.-M., 2009, 84 p.].

Systematic ethanol consumption results in the development of brain activity and central nervous system (CNS) disorders. Complications of alcoholism are demyelination of the neural pathways leading to alcoholic polyneuropathy and cramp provocation. Impairing a normal functioning of the nervous tissue alcohol causes irreversible damage and/or death of the nerve cells. The impact of acute and chronic alcohol intoxication on the human health has not been solved to finality by the modern medicine. Affecting all organs and systems of the body alcohol leads to early invalidization of the young and most able-bodied population.

Despite a wide application of antialcoholic pharmaceutical agents of different pharmacological groups including sedatives, sleeping-draughts, antipsychotics, antidepressants, and so on, in medicine, search for new effective agents for prevention and treatment of chronic alcohol intoxication remains heretofore vital.

Mechanisms of alcohol dependence include failure of functioning dopaminergic and other mediator systems of the brain [Myers R. D. et al. *Neurotransmitter and neuromodulatory mechanisms involved in alcohol abuse and alcoholism: Epitome of cerebral complexity/Neurochemistry International*, 1995, Vol. 26, N. 4, pp. 337-342], humoral and neurotrophic factors [Darcq E. et al. *MicroRNA-30a-5p in the prefrontal cortex controls the transition from moderate to excessive alcohol consumption/Molecular Psychiatry*, 2014, pp. 1-11]. The study of the roles of macro- and microelements supply in forming, preventing and treating alcohol dependency is a perspective direction of investigations, as microelemental status of the body can be regulated in a highly specific way by special preparations containing microelements.

Lithium ions play an important role in the regulation of neuromediator balance, maintenance of neurotrophic factor balance, and many other physiological processes important for CNS. Pharmacological applications of superhigh doses of lithium carbonate in psychiatric disorders have been studied most deeply [Chia-Ming Chang et al. *Utilization of Psychopharmacological Treatment Among Patients With Newly Diagnosed Bipolar Disorder From 2001 to 2010/Journal of Clinical Psychopharmacology*, 2016, Vol. 36, N. 1, pp. 32-44]. However, the spectrum of biological roles of lithium is much wider.

Participation of lithium ions in metabolism of simple sugars (including regulation of insulin secretion) [Zawalich W. S. et al. *Interactions between lithium, inositol and mono-oleoylglycerol in the regulation of insulin secretion from isolated perifused rat islets/Biochemistry Journal*, 1989, Vol. 262, N. 2, pp. 557-561]), in lipid metabolism [Diaz-Sastre C. et al. *Cholesterol and lithium levels were correlated but serum HDL and total cholesterol levels were not associated with current mood state in bipolar patients/Journal of Clinical Psychiatry*, 2005, Vol. 66, N. 3, pp. 399-400], in regulation of arterial pressure [Koda L. Y. et al. *Lithium treatment decreases blood pressure in genetically hypertensive rats/European Journal of Pharmacology*, 1981, Vol. 76, N. 4, pp. 411-415], and in hematopoiesis [Focosi D. et al. *Lithium and hematology: established and proposed uses/Journal of Leukocyte Biology*, 2009, Vol. 85, N. 1, pp. 20-28] has been established. Lithium ions promote inhibition of cyclooxygenase-2, which decreases pyrogenic prostaglandin E2 concentration in the brain and other tissues, and results in anti-inflammatory action of lithium preparations [Phelan K. M. et al. *Lithium interaction with the cyclooxygenase 2 inhibitors rofecoxib and celecoxib and other nonsteroidal anti-inflammatory drugs/Journal of Clinical Psychiatry*, 2003, Vol. 64, N. 11, pp. 1328-1334].

The importance of participation of lithium ions in homeostasis of neuromediators should be especially underlined. Lithium ions are selectively accumulated in CNS and affect essentially homeostasis of many neurotransmitters. Thus, lithium ions influence the metabolism and activity of acetylcholine receptors, activity of acetylcholinesterase, and acetylcholine secretion in the brain cortex [Hillert M. H. et al. *Dynamics of hippocampal acetylcholine release during lithium-pilocarpine-induced status epilepticus in rats/Journal of Neurochemistry*, 2014, Vol. 131, N. 1, pp. 42-52]. In the experiment [Stengaard-Pedersen K. et al. *In vitro and in vivo inhibition by lithium of enkephalin binding to opiate receptors in rat brain/Neuropharmacology*, 1982, Vol. 21, N. 8, pp. 817-823], lithium ions regutated enkephalin levels in the hypophysis. Lithium ions inhibit accumulation of cyclic adenosine monophosphate (AMP) in the brain neurons occurring during adrenergic receptor activation [Ebstein R. P. et al. *The effect of lithium on noradrenaline-induced cyclic AMP accumulation in rat brain: inhibition after chronic treatment and absence of supersensitivity/Journal of Pharmacology and Experimental Therapeutics*, 1980, Vol. 213, N. 1, pp. 161-167].

It is important to note that lithium ions affect dopamine homeostasis [Basselin M. et al. *Chronic lithium chloride administration to unanesthetized rats attenuates brain dopamine D2-like receptor-initiated signaling via arachidonic acid/Neuropsychopharmacology*, 2005, Vol. 30, N. 6, pp. 1064-1075], activity of serotonin receptors [Castro L. et al. *Central 5-HT2B/2C and 5-HT3 receptor stimulation decreases salt intake in sodium-depleted rats. Brain Research*, 2003, Vol. 981, N. 1-2, pp. 151-159], increase the levels of GABA receptors, reduce the activity of signaling cascades activated by NMDA-receptors [Basselin M. et al. *Chronic lithium chloride administration attenuates brain NMDA receptor-initiated signaling via arachidonic acid in unanesthetized rats/Neuropsychopharmacology*, 2006, Vol.

31, N. 8, pp. 1659-1674], inhibit formation of dependence on cannabinoids modulating cAMP, ERK1/2, and GSK3 signaling pathways. Other hormonal effects of lithium are also being studied: the effect of lithium ions on neuroactive steroids and neuroplasticity has been established [Marx C. E. et al. *Neuroactive steroids, mood stabilizers, and neuroplasticity: alterations following lithium and changes in Bcl-2 knockout mice/International Journal of Neuropsychopharmacology*, 2008, Vol. 11, N. 4, pp. 547-552]. All said biochemical mechanisms are impaired in one way or another under the impact of alcohol.

SUMMARY OF THE INVENTION

The present invention solves the task of creating a novel effective agent for prophylaxis of alcoholism complications and treatment of chronic alcoholic intoxication, the said agent is also characterized by low toxicity.

The technical result of the present invention consists in widening the arsenal of agents used for prophylaxis and treatment of chronic alcohol intoxication.

The said technical result is achieved by using lithium ascorbate as such an agent in the dose at least 5 mg/kg.

In one of the embodiments of the present invention, lithium ascorbate is preferably used in the doses of 5 to 30 mg/kg.

A) Aggregation of erythrocytes, pericapillary edema of the grey matter of the forebrain cortex. Hematoxylin and eosin staining. Magnification ×1200.

B) Severe pericellular edema of the brain stem. Impregnation with silver. Magnification ×480.

C) Microfocal hemorrhage in the pyramidal layer of the cerebral cortex. Hematoxylin and eosin staining. Magnification ×120.

D) Acute swelling of the pyramidal nerve cell of the cerebral cortex with a phenomenon of chromotolysis. Nissl staining with toluidine blue. ×1200.

Figure 2:
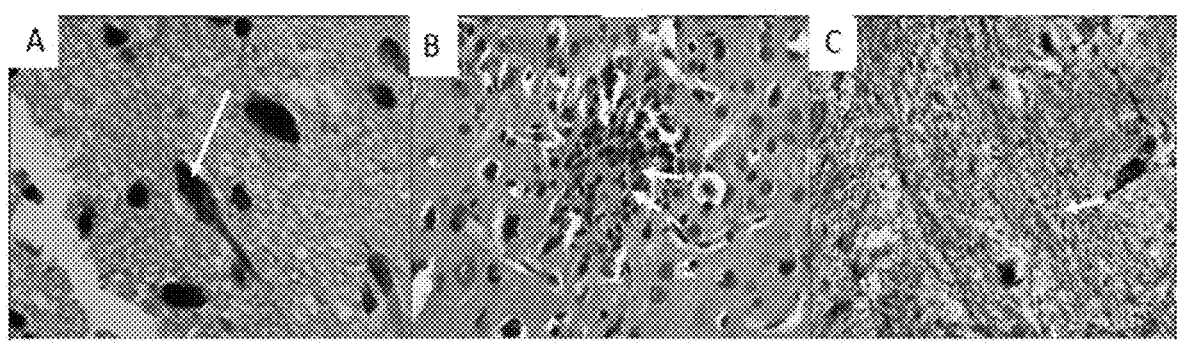

FIG. 2. Irreversible alterations of the cerebral cortex neurons.

A) Lumpy decay of the hyperchromic shrunken neuron. Nissl staining with toluidine blue. Magnification ×1200.

B) Formation of a neurophagic nodule in the cerebral cortex. Hematoxylin and eosin staining. Magnification ×480.

C) Commissural fibers of the cerebral cortex have fuzzy contours with myelin fragments. Silver impregnation. Magnification ×1200.

D) Acute swelling of the cortical pyramidal nerve cell with the phenomenon of chromatolysis. Nissl toluidine blue stain. Magnification ×1200.

Figure 3:
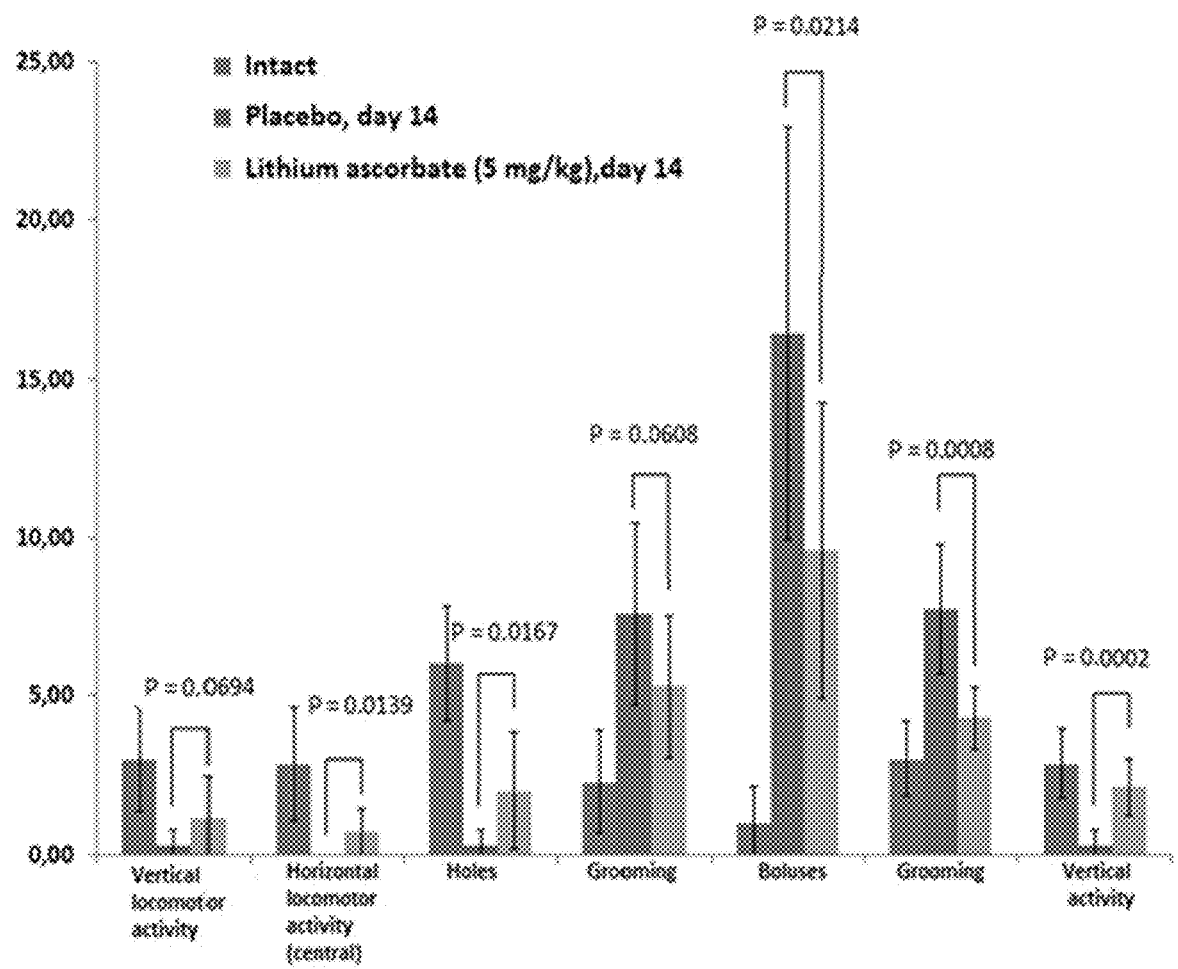

FIG. 3. Indices of neurological tests obtained using the created alcohol intoxication model and prophylactic application of lithium ascorbate in the dose of 5 mg/kg.

Figure 4:
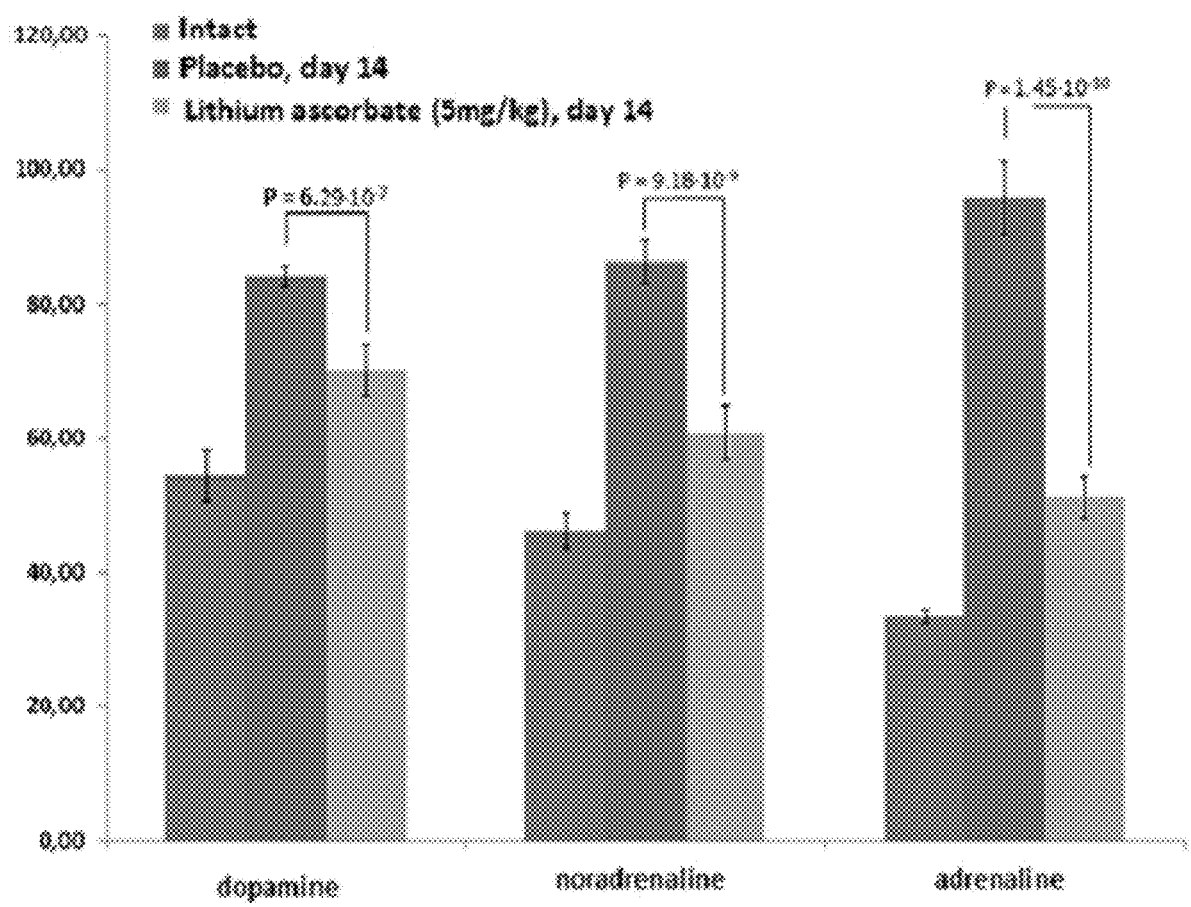

FIG. 4. Biochemical indices obtained using the created alcohol intoxication model and prophylactic application of lithium ascorbate in the dose of 5 mg/kg.

Figure 5:
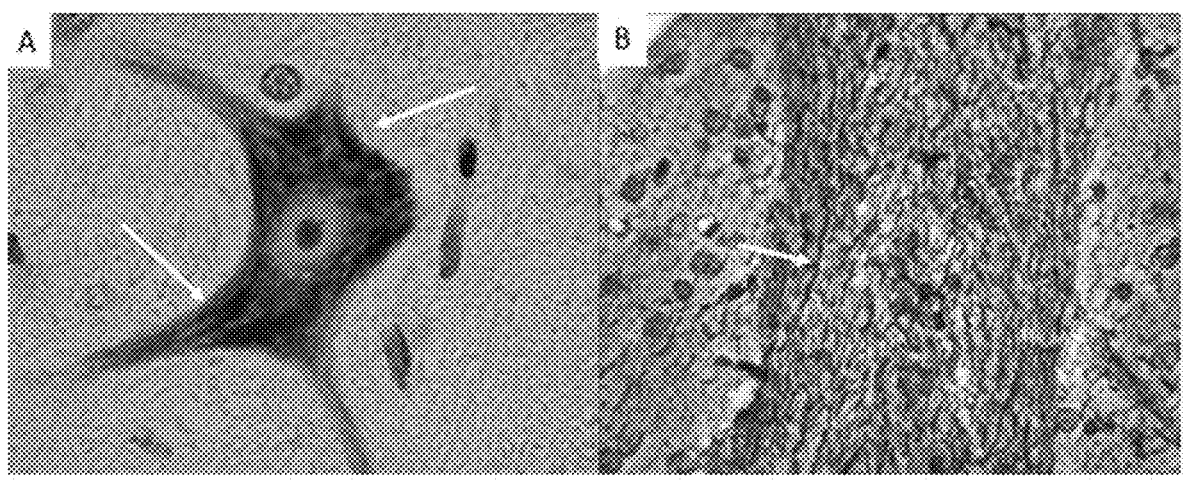

FIG. 5. Histological effects of lithium ascorbate application.

A) Focal fusions of Nissl bodies in the cytoplasm of the pyramidal cell. Nissl staining with toluidine blue. Magnification ×1200.

B) Sharply stained contours of commissural brain fibers with a preserved integrity of myelin sheath. Silver impregnation. Magnification ×1200.

Figure 6:
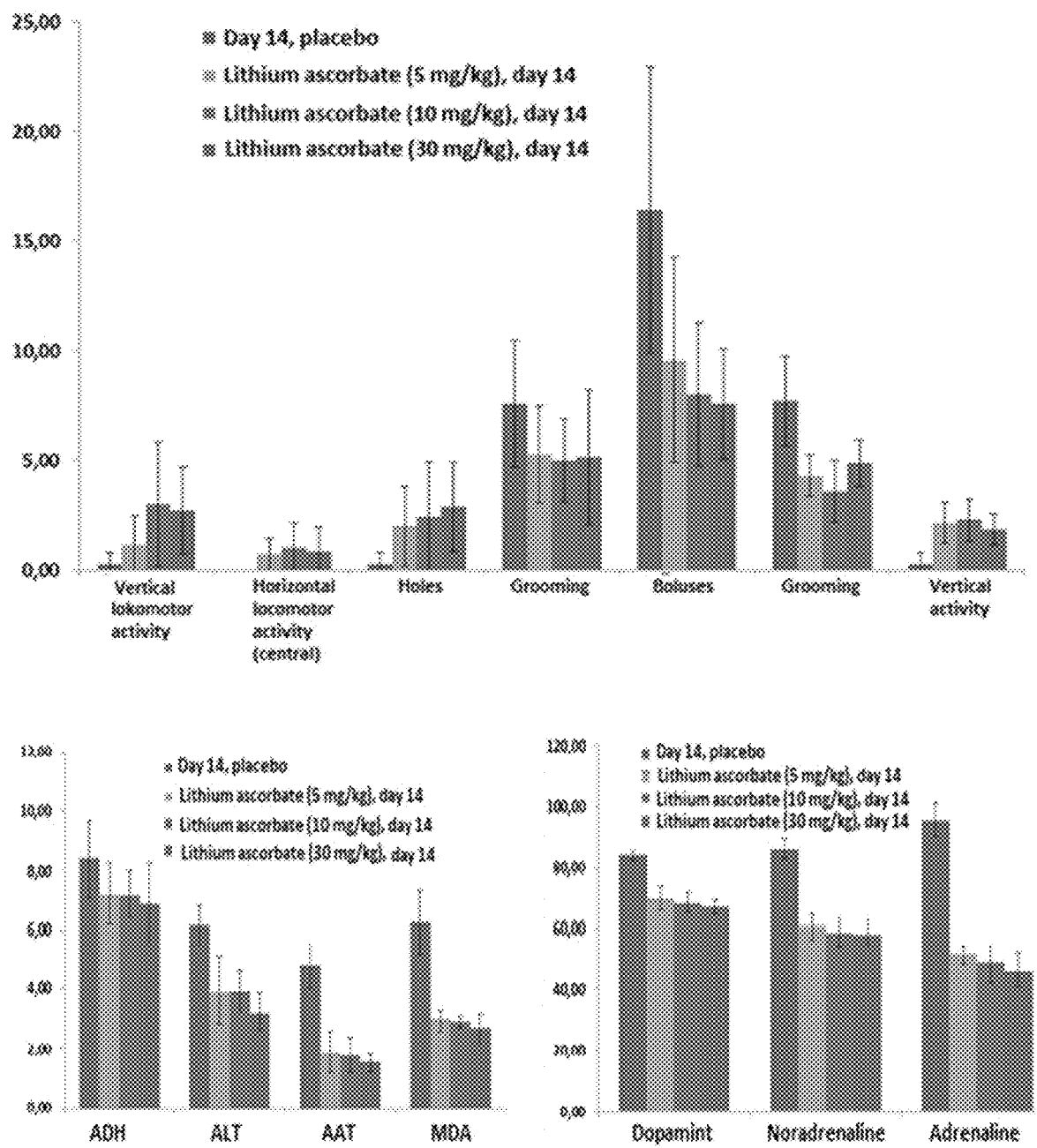

FIG. 6. Dose-dependence of lithium ascorbate prophylactic effects.

Figure 7:
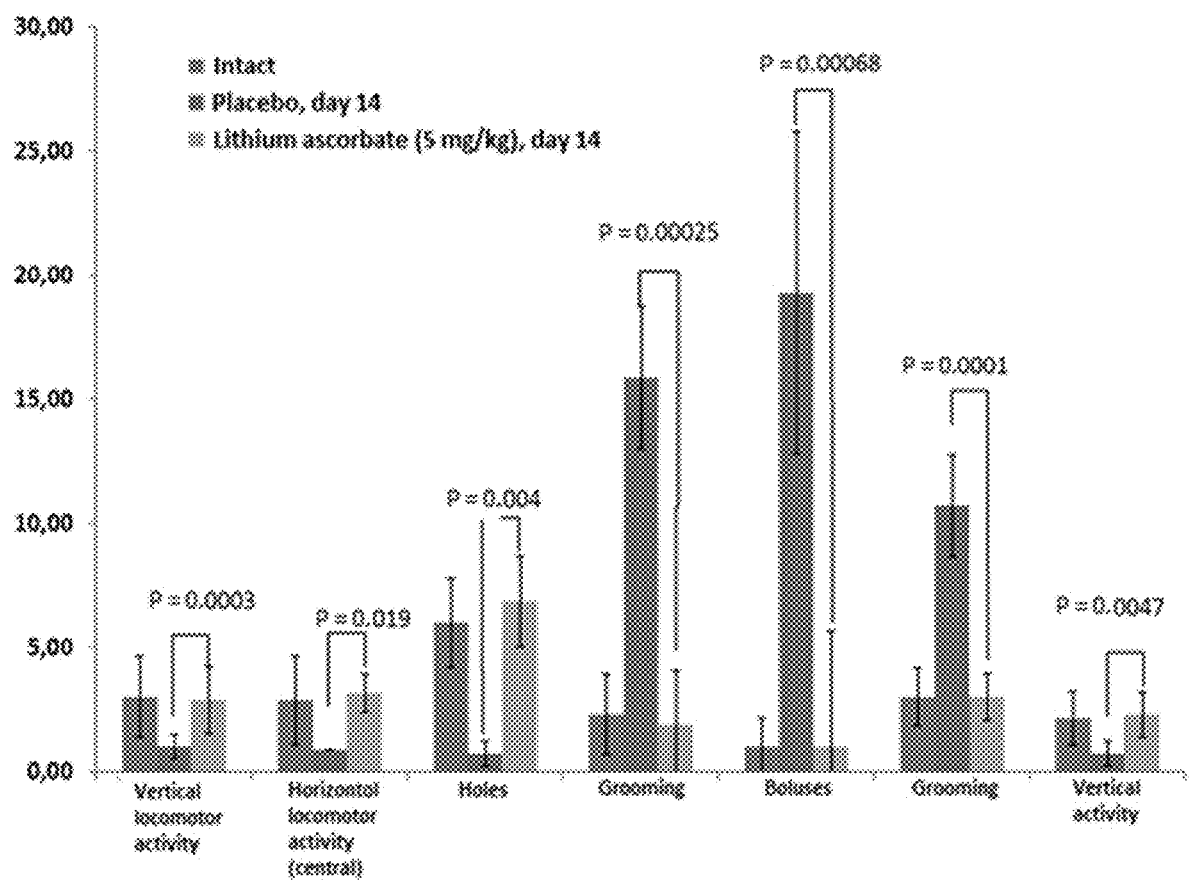

FIG. 7. Indices of neurological tests obtained using the created alcohol intoxication model and therapeutic application of lithium ascorbate in the dose of 5 mg/kg.

Figure 8:
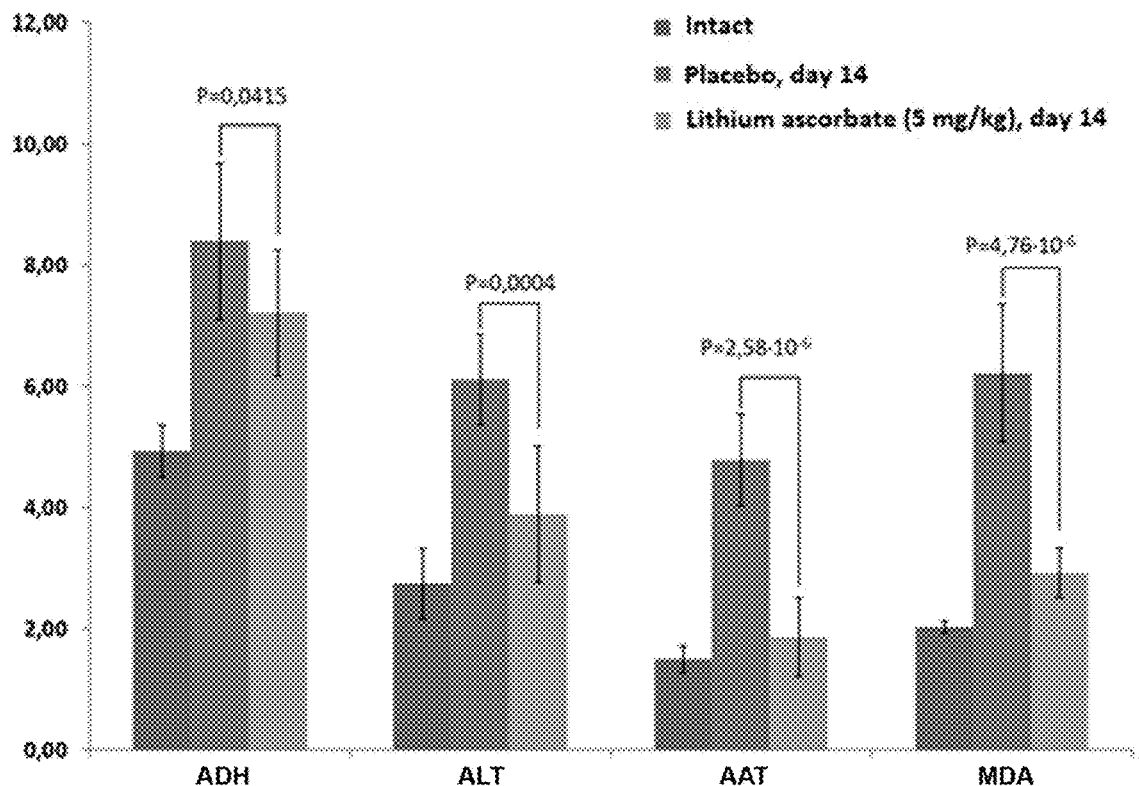
Figure 8:
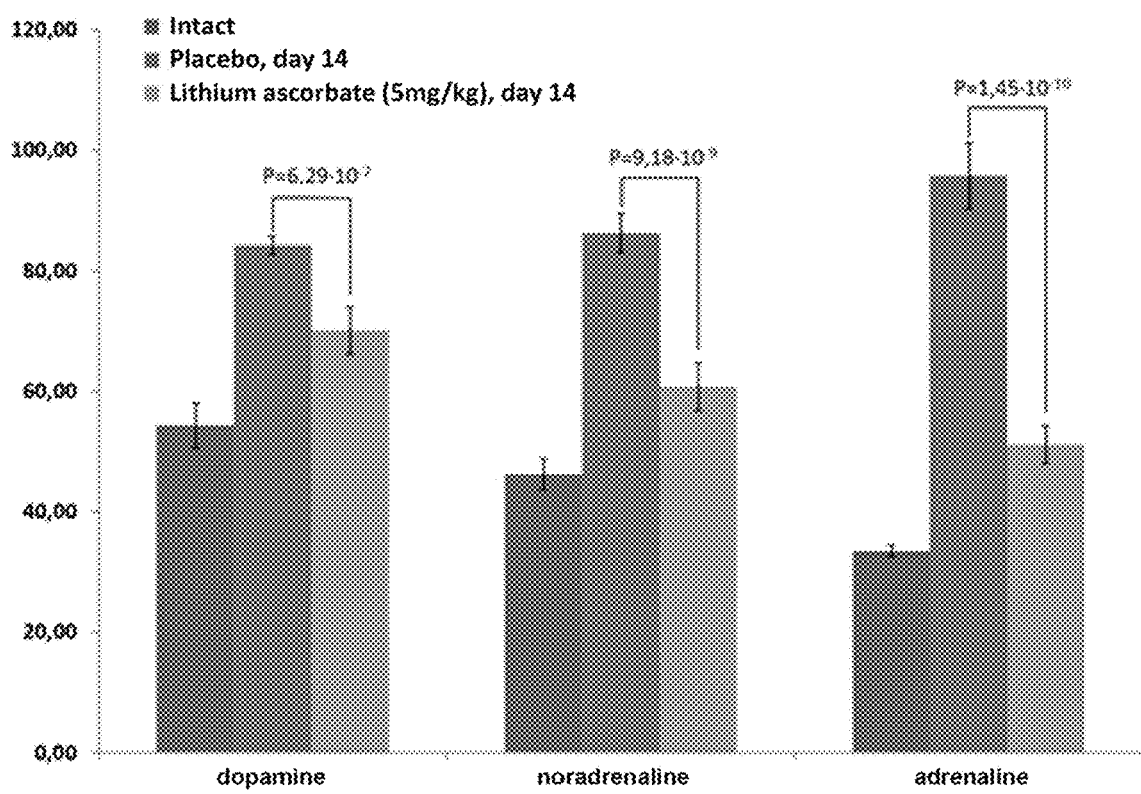

FIG. 8. Biochemical indices obtained using the created alcohol intoxication model and therapeutic application of lithium ascorbate in the dose of 5 mg/kg.

Figure 9:
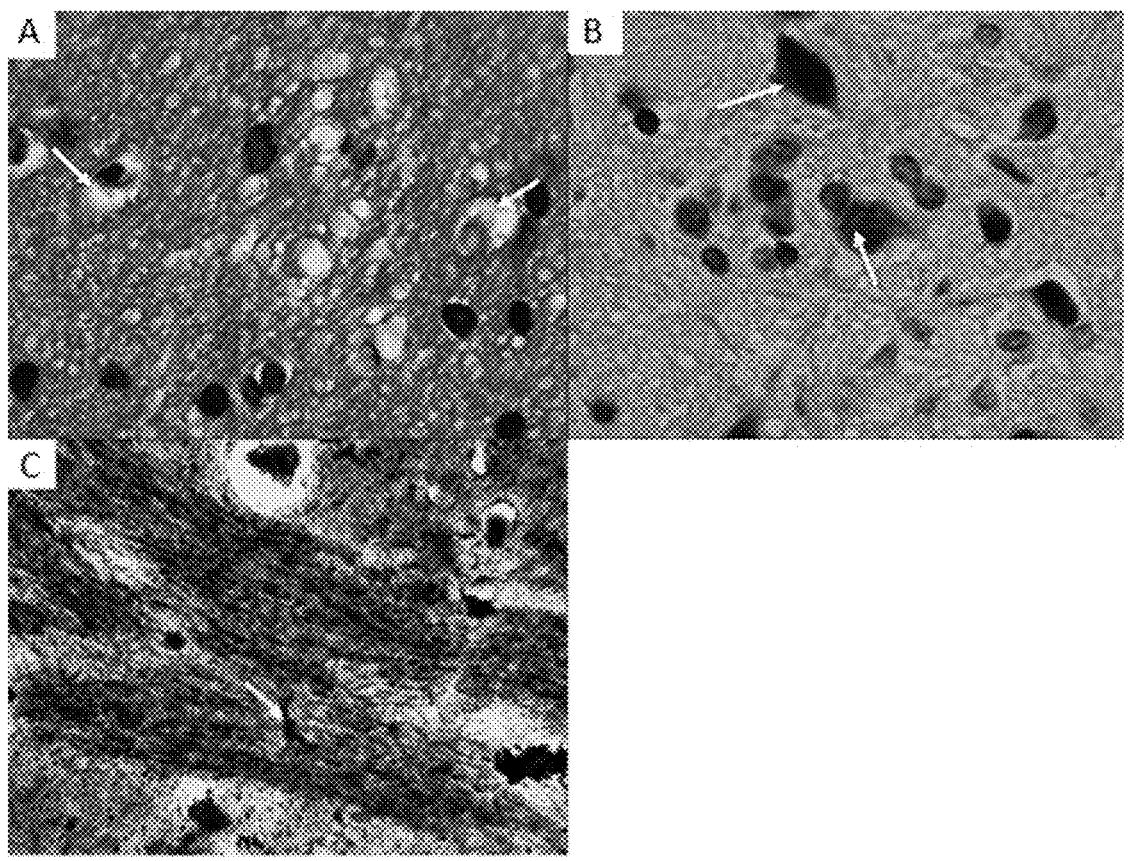

FIG. 9. Therapeutic application of lithium ascorbate: histological picture.

A) Marked pericapillary edema of the nerve tissue. Hematoxylin and eosin staining. Magnification ×1200.

B) Hyperchromatosis, pycnosis of neurocytes. Astrogliocyte hypertrophy. Nissl staining with toluidine blue. Magnification ×1200.

C) Focal demyelination of the brain nerve fibers. Impregnation with silver. Magnification ×1200.

Figure 10:
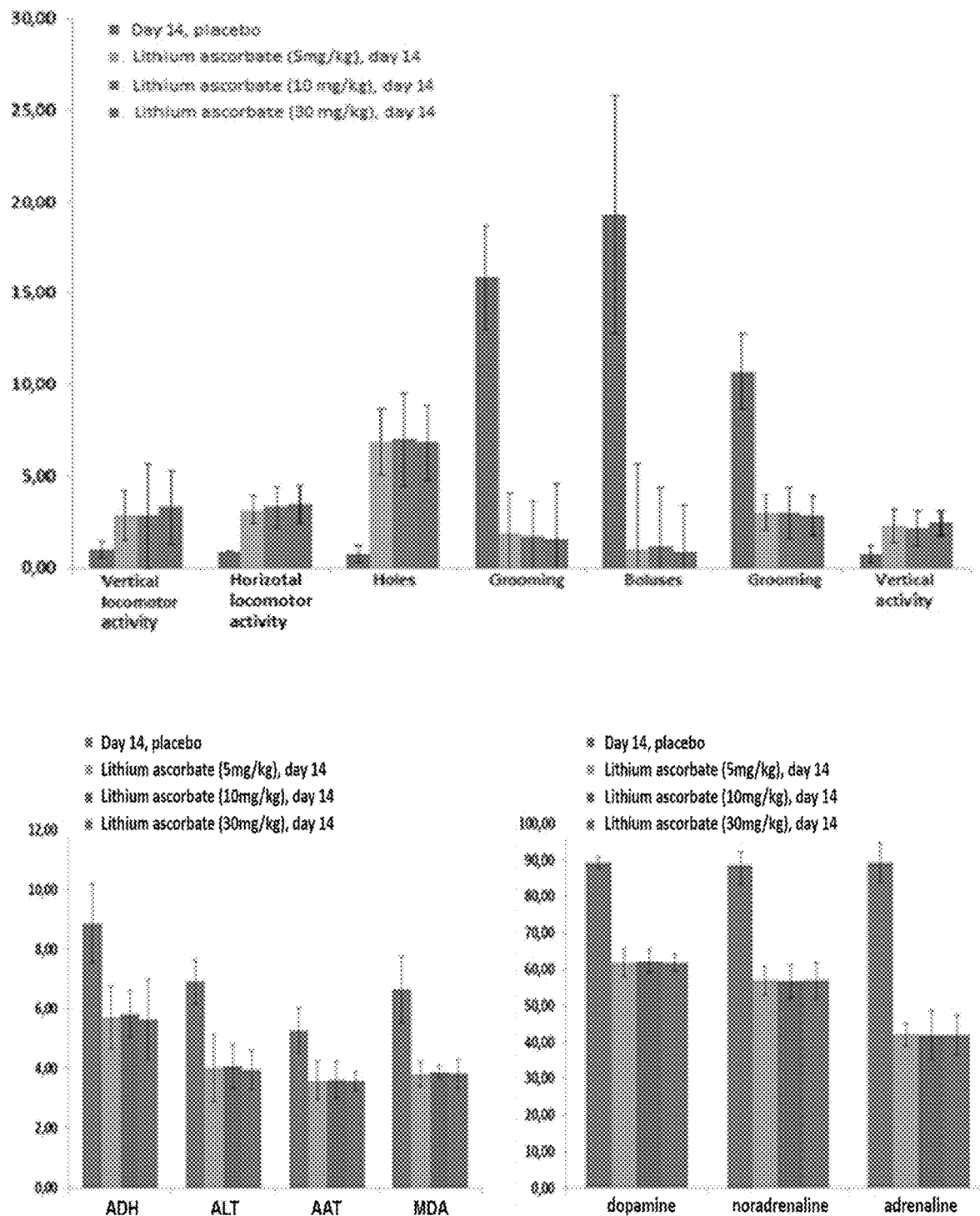

FIG. 10. Dose-dependence of lithium ascorbate therapeutic effects.

DETAILED DESCRIPTION OF THE INVENTION

Lithium ascorbate is known [Ostrenko K. S. et al. *Determination of acute toxicity and negative effect of high doses of lithium ascorbate on Wistar rats during long-term application/Pharmacokinetics and pharmacodynamics*, 20161, No 4, p. 44-54] to be referred to the compounds of toxicity Class 5, i.e. it is practically nontoxic.

Tests confirming the possibility of using lithium ascorbate as an agent for prophylaxis and treatment of chronic alcohol intoxication have been performed, which is illustrated by an example below. The effect of lithium ascorbate was investigated on the model of chronic alcohol intoxication. Said investigation included determination of minimally effective doses of lithium ascorbate preventing the development of alcoholic dependency in Wistar rats, and efficacy of alcoholic intoxication therapy.

Example of an embodiment of the invention.

Materials and Methods. White Wistar male rats weighing 200-250 g (n=168) were used as a model object. The investigation was approved by ethical committee of Federal State Budgetary Educational Institution of Higher Professional Education "Ivanovo State Medical Academy", the Ministry of Health of the Russian Federation" on Mar. 15, 2016; all procedures and experiments on rats were conducted in compliance with the international rules of treating animals used for scientific purposes. Animals were housed in equal rooms in cages of 7 rats in each at 19-21° C. Animals were given 40-50 g of a mixed fodder per animal every day.

Creating a model of alcohol dependence. The criterion for selecting rats, along with the absence of obvious abnormalities in the state and behavior, was an initial preference for 6% ethyl alcohol over tap water. To determine this preference, a preliminary experiment was conducted during 3 days in the individual cages with a free access to both liquids. Once a selection has been done, 6% ethyl alcohol was offered as the only source of liquid, a week later the concentration of alcohol was increased to 15%. After 2 weeks, alcohol was replaced by tap water.

Preparation dosage and application. The experiment was carried out in two series «prophylaxis» and «treatment» with four groups in each series: (1) dose 30 mg/kg (experimental group 1), (2) dose 10 mg/kg (experimental group 2), (3) dose 5 mg/kg (experimental group 3), (4) placebo group. In the experiments of "prophylaxis" series, the preparation was introduced concurrently with model creation, while in the experiments of "treatment" series it was done after model creation. Each group contained 21 animals. Said preparation was introduced intragastrically via a probe once a day in volume of 0.5 ml per each animal for 14 days.

Neurological testing. A general assessment of somatic and neurological status of animals was performed in all examined groups. The level of anxiety, adaptogenicity and negative effect of alcohol on the CNS was evaluated by observing animal behavior in the open field (OFT) and elevated plus maze (EPMT) tests 7 and 14 days after lithium ascorbate introduction.

In the open field test (OFT), vertical activity, horizontal activity, frequency of dipping into the holes (a hole exploratory test or "burrow reflex"), grooming frequency, and frequency of central zone entries were registered. In OFT, an animal was placed in one and the same square located near the wall. An exposure time for each animal in the model was 5 min. A round OF represented an arena 1 m in diameter and a wall of 0.4 m height with the floor divided into sectors. Three zones were marked in the open field: central, intermediate (6 sectors), peripheral (12 sectors). Two 60 W lamps were located at a height of 1.5 m from the chamber floor over the central field segments. Horizontal activity in the central and peripheral zone, vertical activity, grooming frequency, frequency of defecation, burrow reflexes were fixed during the test. The walls and floor were treated with a wet and dry cloth after each animal.

The time spent in the open and closed arms and in the maze center, duration of grooming in the closed arm, a number of grooming episodes in the closed arm were registered during the elevated plus maze test (EPMT). The tested object was placed in the center of EPM with its nose towards the open arm. The time of testing the animals in the EPM amounted to 5 min. The apparatus used in the test consisted of two arms with an open area at the site of their crossing. One of the maze arms had closed compartments. The maze was installed at a height of 1 m from the floor. The time spent in the open and closed arm, grooming frequency, and rearing frequency were registered.

Measurement of biochemical indices. Biochemical indices of alanine transaminase (ALT), aspartate aminotransferase (AAT), gamma-glutamyl transpeptidase (GGT), malondialdehyde (MDA), dopamine, noradrenaline, adrenaline, serotonin in blood serum, and alcohol dehydrogenase (ADH) in hepatic cells were determined in animals of all groups on day 0 and day 14. Blood was taken from the sublingual vein by cutting frenum of the tongue. Serum was obtained from the whole blood in compliance with the instructions [Sidorov Evgeny *"Guidelines for designation and interpretation of biochemical blood tests"*, 2015]. Tests were performed using automated Konelab-20i biochemical analyzer (ThermoFisher Scientific, Finland-USA). Hepatic cells for determining alcohol dehydrogenase (ADH) were harvested after the experiment. ADH activity in hepatocytes was assessed by a photometric method.

ALT and AAT in μmol/ml/h were determined using automated photometric CHEM WELL 2910 (C) analyzer (Combi, USA), gamma-glutamyl transpeptase (GGT) in Units/l was evaluated by a kinetic colorimetric method. Standard kits "ALT-UTS", "ACT-UTS" (Ailiton, Rissia), and "Human" kits (Germany) for determining GGT were used [O'Connor K. At al. *The Triple-Negative Test for Alcohol Dependence: A Reliability Study/Am Surg.* 2016, June; 82(6), P. 120-122.; Goryushkin I. I. *Mechanisms of alcogolism: regulating and structural relations (pathogenesis, diagnosis, treatment), monograph*, M.:Sputnik+, 2008.- pp. 51-61.], MDA in nmol/ml [Mihara M. et al. *Thiobarbituric acid value on fresh homogenate of rat as a parameter of lipid peroxidation in aging, CCl4 intoxication, and vitamin E deficiency/Biochem Med.*, 1980, V. 23, N.3, pp. 302-311], and ADH in nmol/mg protein/min [Bochkaryova A. V. et al. *Change of alcohol dehydrogenase activity of the rat hepatic cells under the action of ethanol and heparin/ Proceedings of Nizhny Novgorod Lobachevsky University*, 2010, Vol. 2, No 2, pp. 490-493] using NanoDrop™ 2000 microspectrophotometer. Serotonin was assayed by Michael's method. Catecholamines (dopamine, noradrenoline, adrenaline) in nmol/ml were assessed using Water 590 fluid chromatographer with amperometric detector (Science and Production Association (SPA) Chimautomatics, Russia), (main electrode material—glassy carbon), Ascenic C18 column (5 μm, 4.6×250 mm). Electrophoretic evaluation was performed using a capillary electrophoresis system Capel-105 (OOO NPF Lumex, Russia) with a spectrophotometric detector, unmodified quarzt capillary with 60 cm total length, 50 cm effective length, 50 μm inner diameter.

Histological analysis of the nervous tissue. The brain after craniotomy was wholly removed and fixed in a 10% solution of neutral formalin, in 24 hours a zone of precentral gyrus of the forebrain was exposed by frontal incisions. Preparation of nerve tissue specimens was performed according to a standard procedure (dehydration in ethyl alcohol, xylene) with subsequent fabrication of paraffin blocks. Histological sections of 6 μm thick made on a sliding Microm microtome were stained with hematoxylene and eosin. Section duplicates were Nissl-stained with a reagent kit (Biovitrum Co.) and impregnated with silver. Histological sections were morphometrically examined using BioVision image analyzer (Austria) for counting damaged neurocytes of the pyramidal layer of the forebrain cortex in 10 various fields of vision with subsequent statistical processing of the results. Microphotographs were obtained with the help of the research Micros microscope and DCM 900 digital ocular camera.

Data processing. The results were processed using Excel 2003 and Statistica 8.0 software packages. The significance of differences between the groups was determined by nonparametric U-criterion—Wilcoxon-Mann-Whitney test.

The model of alcohol intoxication. Intact animals demonstrated normal indices during neurological testing (Table 1), had a shining smooth fur, were active.

TABLE 1

Behavior of intact animals

Behavior of animals in the open field test (OFT)

| Groups | Vertical locomotor activity | Horizontal locomotor activity | | Frequency of dipping into the hole | Grooming frequency (times) | Number of boluses (pcs) |
|---|---|---|---|---|---|---|
| | | central | peripheral | | | |
| Group 1 (0 mg/kg) | 3.0 | 2.9 | 12.3 | 6.0 | 2.3 | 1.0 |
| Group 2 (10 mg/kg) | 2.9 | 2.6 | 12.1 | 6.1 | 1.9 | 0.9 |
| Group 3 (5 mg/kg) | 3.2 | 3.0 | 13.1 | 6.5 | 2.6 | 1.2 |
| control | 2.9 | 2.4 | 11.9 | 6.3 | 2.0 | 1.0 |

Behavior of the animals in the elevated plus maze test (EPMT)

| | Time spent in the open arm (s) | Time spent in the closed arm (s) | Grooming frequency (times) | Vertical activity |
|---|---|---|---|---|
| Group 1 (30 mg/kg) | 40.15 | 258.34 | 3.04 | 2.3 |
| Group 2 (10 mg/kg) | 42.24 | 244.13 | 2.95 | 1.94 |
| Group 3 (5 mg/kg) | 50.12 | 246.16 | 3.10 | 2.8 |
| control | 46.24 | 250.45 | 3.01 | 2.1 |

Replacement of water by 6% and later by 15% alcohol solution resulted in two weeks in the impairment of behavioral reactions in the rats. In the rats from the control group receiving an alcohol solution only, increase of horizontal peripheral activity and complete exclusion of entries to the center were noted in the open field and elevated plus maze tests. Dull fur with foci of alopecia was noted in the animals. Animals moved chaotically along the wall not exhibiting exploratory behavior and searching skills. It may speak of a prevailing sense of anxiety and fear intercurrently with alcohol intoxication. Frequency of defecation and grooming acts increases in such condition. Changes of indices of neurological and biochemical blood testing occurring during model creation are presented in more detail in Table 2.

TABLE 2

Changes of indices of neurological and biochemical blood testing in chronic alcohol intoxication

| Indices | M, Day 0 | ±m | M, Day 14 | ±m | P |
|---|---|---|---|---|---|
| Open field test (OFT) | | | | | |
| Horizontal locomotor activity (peripheral) | 13.00 | 1.63 | 19.00 | 6.06 | 0.013182 |
| Vertical locomotor activity | 3.00 | 1.63 | 0.29 | 0.49 | 0.000601 |
| Horizontal locomotor activity (central) | 2.86 | 1.77 | 0.00 | 0.00 | 0.00055 |
| Frequency of dipping into the hole (times) | 6.00 | 1.83 | 0.29 | 0.49 | 1.88E−06 |
| Grooming frequency (times) | 2.29 | 1.60 | 7.57 | 2.88 | 0.000569 |
| Number of boluses (pcs) | 1.00 | 1.15 | 16.43 | 6.50 | 2.36E−05 |
| Elevated plus maze test (EPMT) | | | | | |
| Grooming frequency (times) | 3.00 | 1.15 | 7.71 | 2.06 | 9.66E−05 |
| Vertical activity | 2.86 | 1.07 | 0.29 | 0.49 | 4.31E−05 |
| Time spent in the open arm (s) | 42.24 | 2.37 | 0.55 | 0.21 | 3.25E−15 |
| Time spent in the closed arm (s) | 250.74 | 4.80 | 299.31 | 0.34 | 2.32E−12 |
| Biochemical indices | | | | | |
| ADH | 4.93 | 0.43 | 8.40 | 1.29 | 1.04E−05 |
| ALT | 2.74 | 0.57 | 6.12 | 0.74 | 2.9E−07 |
| AAT | 1.50 | 0.22 | 4.78 | 0.76 | 6.11E−08 |
| GGT | 75 | 12 | 56 | 18 | 2.11E−05 |
| MDA | 2.04 | 0.10 | 6.22 | 1.13 | 2.16E−07 |
| dopamine | 54.30 | 3.78 | 84.16 | 1.56 | 1.04E−10 |
| noradrenaline | 46.23 | 2.55 | 86.22 | 3.30 | 4.26E−12 |
| adrenaline | 33.40 | 0.95 | 95.76 | 5.47 | 6.56E−13 |
| serotonin | 1070.29 | 9.07 | 857.12 | 5.23 | 5.5E−16 |

Figure 1:
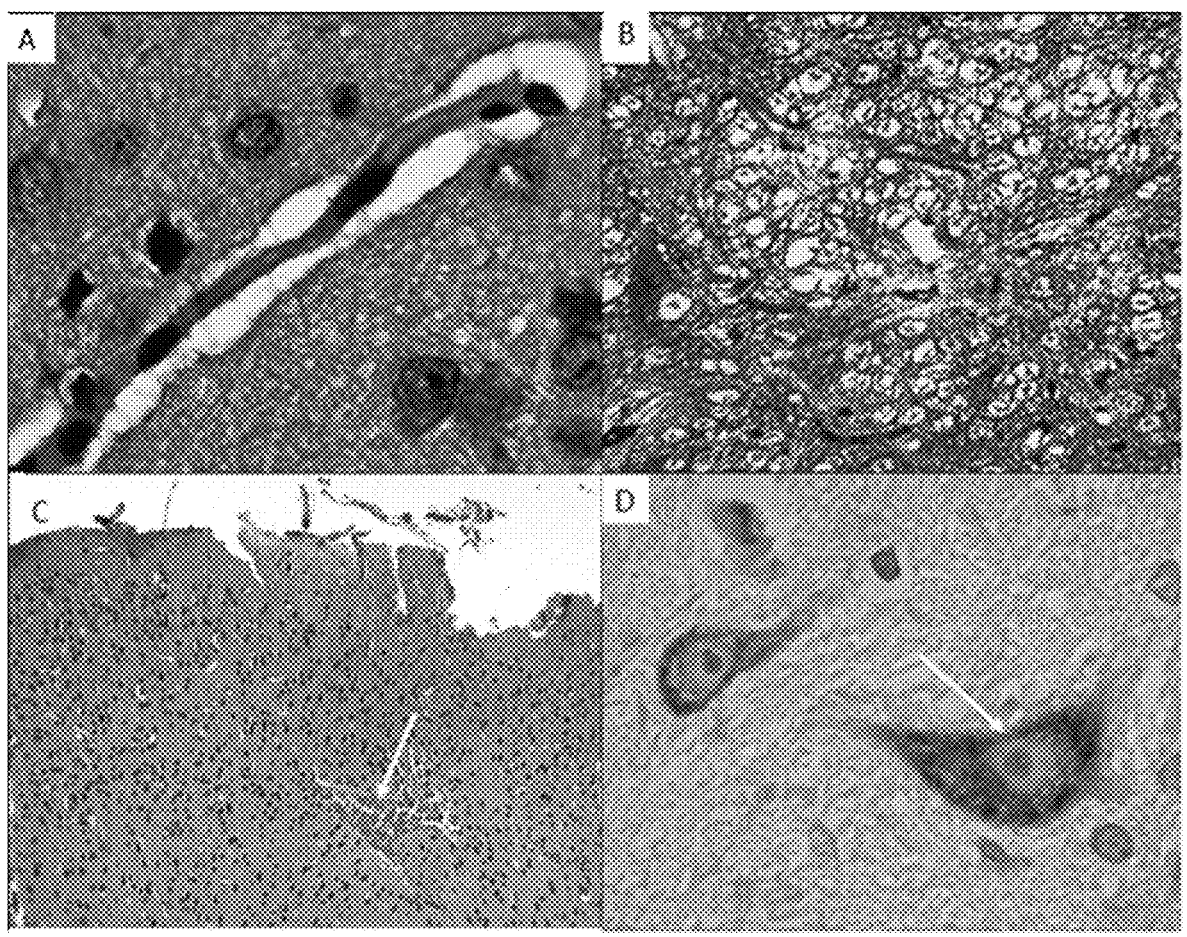
FIG. 1. Histology of the nerve tissue in the model of alcohol intoxication.

FIG. 1 demonstrates the histology of the nerve tissue in the model of alcohol intoxication. Histological analysis showed that during modeling of chronic alcohol intoxication disorders of blood circulation, which were characterized by hemostasis in the capillaries and venules with the development of prominent perivascular edema of the nerve tissue, were found in all observations of the control group (FIG. 1A). In hemocirculation disorder at the level of microcirculatory bed (MCB), pericellular edema of the white substance of the cerebral hemispheres and brain stem grew gradually (FIG. 1B). Microfocal hemorrhages were revealed in the cerebral cortex and the stem part of the brain (FIG. 10). Toxic damage of the cerebral cortex neurocytes was characterized by acute swelling of the pyramidal cells with rounding of the cellular body, axon swelling, homogenization of the cytoplasm with Nessl granulation disappearance, impairment of the nucleus contours (FIG. 1D).

Irreversible alterations of the cerebral cortex neurons (FIG. 2) were accompanied by hyperchromatosis, neurocyte pycnosis with a subsequent lumpy decay and formation of neurophagic nodules (FIG. 2A, FIG. 2B). When studying the brain zones containing conducting pathways, swelling of the myelin fibers with irregular myelin distribution and varicose thickenings along the fibers were detected (FIG. 2C). Thus, during creation of the alcohol intoxication model, marked neurological and biochemical disorders are noted, which correspond to a severe pathology of the nerve tissue.

Results of the prophylactic application of lithium ascorbate in alcohol intoxication. Combined introduction of alcohol solution and lithium ascorbate in various dosages changed markedly the picture of intoxication in the tested animals. The course introduction of lithium ascorbate in various dosages during 2 weeks to the rats suffering from alcoholic intoxication increased vertical activity and other test indices (FIG. 3). The frequency of central square entries and burrow reflex index in the animals of the given groups was comparable with the indices for healthy animals. Effective prophylaxis of neurological disorders was noted beginning with a 5 mg/kg dose of lithium ascorbate.

Long-term alcohol intoxication caused increase of catecholamine concentration (dopamine, noradrenoline, adrenaline) in the blood, which designates a prominent activation of sympatico-adrenal system (FIG. 4). Application of lithium ascorbate together with alcohol inhibited the increase of catecholamine content in the animal blood and prevented the negative effect of alcohol. The efficacy of lithium ascorbate showed itself in activation of ADH in the liver, which corresponds to a more rapid elimination of ethanol.

Introduction of ethanol is known [Shabanov P. D. et al. *Biology of alcoholism/SPb.*: published by "Lan", 1998.-272 p.] to cause activation of lipid peroxidation (LPO) in the cell membranes of the liver, brain and heart, which results in accumulation of primary and secondary products of oxidation in the biological liquids. In the course of the investigation it was established that alcohol induced a significant rise of MDA in the blood serum. Introduction of lithium ascorbate decreased MDA levels (FIG. 4), which corresponded to LPO inhibition.

Thus, lithium ascorbate significantly activates neuroadaptation mechanisms, normalizes behavior reactions in the open field (OFT) and elevated plus maze (EPMT) tests. These results agree with the findings of the histological analysis of the brain tissue specimens.

Prophylactic use of lithium ascorbate in chronic alcohol intoxication essentially attenuates histological manifestations of cerebral ischemia. Circulation disorder of the nerve tissue were characterized by focal hemostasis in the capillaries and moderately marked pericapillary edema of the cortex nerve tissue, white substance of the cerebral hemispheres, and brain stem in all groups of animals receiving lithium ascorbate compared to the placebo group.

It is important to note that a considerable part of the cortex neurocytes and subcortex nuclei was characterized by reversible alterations, which displayed themselves by dispersion and indistinct contours of tigroid, focal fusion of Nissl bodies in the cytoplasm, moderately marked swelling of the nucleus and axonal process (FIG. 5A). Macroglial reaction of the nerve tissue was minimal and was in the form of periarteriolar astrocyte edema. Impregnation of the brain pathways with silver showed preservation of myelin sheaths of the nerve fibers, which had sharp contours (FIG. 5B).

The morphometric analysis showed that in the group of animals receiving lithium ascorbate in a dose of 5 mg/kg an amount of the damaged cortex cells was 18.5%, while in the placebo group the amount of the damaged cells was equal to 34.8% in the presence of significant morphological signs of irreversible neurocyte death.

The analysis of the effects of different lithium ascorbate doses for prophylactic application showed that an adequate efficacy of lithium ascorbate is noted already at a dose of 5 mg/kg. Higher doses did not cause any significant increase of lithium ascorbate effect on the tested indices (FIG. 6).

The results of using lithium ascorbate for alcohol intoxication treatment. In the series of «treatment» experiments lithium ascorbate (in doses of 5, 10, 30 mg/kg) was started to be introduced immediately after alcohol solution withdrawal. "Treatment" represents a more rigid model of alcohol intoxication for evaluation of the preparation efficacy. In the placebo group, a prominently expressed abstinence was observed in the form of aggressiveness especially after feeding, mood swings within a short time period after alcohol solution withdrawal. Sharp and sudden attacks of aggression changed into a stupor-like state; occasional cramps were noted in the animals. The animals looked exhausted, fell into superficial light sleep. After awakening, the animals showed again the signs of aggressiveness, fought, refused to drink water, bit drinking dishes. Introduction of lithium ascorbate reduced the number of aggressive incidents. A more profound and prolonged sleeping was observed in the animals, they fell into a stupor not so often. No cramps were noted during lithium ascorbate intake. Testing according to the scales of the open field (OFT) and elevated plus maze tests (EPMT) showed a significant improvement of the state (Table 3, FIG. 7) confirmed by the results of the biochemical tests (FIG. 8).

TABLE 3

Animal behavior in the OF and EPM tests after 7 days of lithium ascorbate introduction

Animal behavior in the open field test (OFT)

| Groups | Vertical locomotor activity | Horizontal locomotor activity | | Frequency of dipping into the hole (times) | Grooming frequency (times) | Number of boluses (pcs) |
| --- | --- | --- | --- | --- | --- | --- |
| | | central | peripheral | | | |
| Group 1 (30 mg/kg) | 1.6 | 1.9 | 17.0 | 2.0 | 5.9 | 12.2 |
| Group 2 (10 mg/kg) | 1.4 | 1.8 | 17.9 | 1.9 | 6.3 | 12.6 |
| Group 3 (5 mg/kg) | 0.9 | 1.0 | 19.3 | 1.1 | 8.9 | 15.1 |
| Control | 0 | 0 | 4.7 | 0 | 17.8 | 24.4 |

Animal behavior in the elevated plus maze test (EPMT)

| | Time spent in the open arm (s) | Time spent in the closed arm (s) | Grooming frequency (times) | Vertical activity |
| --- | --- | --- | --- | --- |
| Group 1 (30 mg/kg) | 38.26 | 259.01 | 5.8 | 1.7 |
| Group 2 (10 mg/kg) | 34.81 | 265.19 | 6.3 | 1.5 |
| Group 3 (5 mg/kg) | 27.73 | 270.67 | 9.1 | 0.8 |
| Control | 0 | 299.71 | 14.5 | 0 |

Thus, a medical application of lithium ascorbate in various doses facilitates quicker restoration of the rat organisms after alcohol intoxication. In the groups received lithium ascorbate animals adapted faster to the absence of alcohol in the diet, more rapidly restored their behavior and explorative reflexes.

The histological analysis showed that in case of using lithium ascorbate with a therapeutic purpose, disorders of the nervous tissue circulation were characterized by a less degree of diffuse and focal hemostasis in the capillaries compared to the placebo group. The brain specimens of the rats received lithium ascorbate were characterized by a moderate dilatation and venule hyperemia, less pronounced edema of the nerve tissue of the cortex and white substance of the cerebral hemispheres and brain stem (FIG. 9A). In the brain specimens of these animals, microfocal rather than macrofocal diapedetic hemorrhages were found in the cerebral cortex (just as in the placebo group). In the lithium ascorbate groups, only single neurocytes with slight damages were detected. They were seen as diffuse and fuzzy tigroid contours, focal fusion of Nissl bodies in the cytoplasm and a moderate swelling of the nucleus (FIG. 9B). The state of the brain pathway system in the animals receiving placebo was characterized by a focal swelling of the myelin fibers with a nonuniform distribution of myelin, which gave a picture of fuzzy contours when silver impregnated (FIG. 9C). Structural changes of the brain nerve fibers in the group received lithium ascorbate were limited by local edema of the nerve fibers with complete preservation of the myelin sheath.

The analysis of the effect of different doses of lithium ascorbate used for treatment purposes showed that an adequate efficacy of lithium ascorbate was noted already at a dose of 5 mg/kg. Higher doses led to insignificant increase of lithium ascorbate effect on the tested indices after 7 days of the experiment and the efficacy equalized on day 14 of its intake (FIG. 10).

A long-term effect of alcohol results in a deviant behavior in the animals, increases aggression, causes irreversible degenerative alterations in the liver, activates sympatico-adrenal system. The created model of chronic alcohol intoxication had distinct characteristic morphological damages in the liver, brain, conductive neural pathways in all cases of observations.

As the result of the investigation it has been established that lithium ascorbate was effective in therapy and prophylaxis of alcoholic intoxication consequences. Indices of neurological tests and biochemical blood analyses have significantly improved already at a dose of lithium ascorbate of 5 mg/kg.

Lithium ascorbate activates adaptive mechanisms normalizing behavioral reactions in the open field and elevated plus maze tests. Cognitive brain functions can improve, in particular, by inhibiting lipid peroxidation and activating the antioxidative system. Besides, lithium ascorbate prevents activation of the sympatico-adrenal system with ethanol and accelerates elimination of ethanol from the blood irrespective of the dosage. The histological analysis showed that application of lithium ascorbate minimized ischemic damage of neurocytes to the level of reversible state and preserved myelin sheathes of the conducting neural pathways. On the whole, application of lithium ascorbate promotes abstinent syndrome arrest, blocks cramp occurrence, and contributes to animal survival. Activating defense and adaptive mechanisms of the organism in chronic alcohol intoxication lithium ascorbate inhibits demyelinization, irreversible degenerative alterations of the nerve tissue.

The invention claimed is:

1. A method for treating a subject suffering from alcoholism or alcohol intoxication, comprising administering to the subject an effective amount of a composition comprising lithium ascorbate, whereby the administration of the composition treats alcoholism or alcohol intoxication in the subject,
   wherein the effective amount of the composition is determined by the following dosage of lithium ascorbate: at least 0.5 mg lithium ascorbate per 1 kg of the subject body mass daily.

2. The method according to claim 1, wherein the effective amount of the composition is determined by the following dosage of lithium ascorbate: from 0.5 to 30 mg lithium ascorbate per 1 kg of the subject body mass daily.

3. The method according to claim 1, wherein prior the administration, demyelinating complications in neurons are found or suspected in the subject.

4. A method for prevention of alcoholism or alcohol intoxication in a subject, comprising administering to the subject an effective amount of a composition comprising lithium ascorbate, whereby the administration of the composition prevents alcoholism or alcohol intoxication in the subject,
   wherein the effective amount of the composition is determined by the following dosage of lithium ascorbate: at least 0.5 mg lithium ascorbate per 1 kg of the subject body mass daily.

5. The method according to claim 4, wherein the effective amount of the composition is determined by the following dosage of lithium ascorbate: from 0.5 to 30 mg lithium ascorbate per 1 kg of the subject body mass daily.

6. A method for alleviating symptoms of alcoholism or alcohol intoxication in a subject suffering from alcoholism or alcohol intoxication, comprising administering to the subject an effective amount of a composition comprising lithium ascorbate, whereby the administration of the composition alleviates symptoms of alcoholism or alcohol intoxication in the subject,
   wherein the effective amount of the composition is determined by the following dosage of lithium ascorbate: at least 0.5 mg lithium ascorbate per 1 kg of the subject body mass daily.

7. The method according to claim 6, wherein the effective amount of the composition is determined by the following dosage of lithium ascorbate: from 0.5 to 30 mg lithium ascorbate per 1 kg of the subject body mass daily.

* * * * *